United States Patent [19]

Baba

[11] Patent Number: 4,466,444
[45] Date of Patent: Aug. 21, 1984

[54] ULTRASONIC DIAGNOSTIC APPARATUS

[75] Inventor: Kazuo Baba, Tokyo, Japan

[73] Assignee: Olympus Optical Co., Ltd., Tokyo, Japan

[21] Appl. No.: 377,025

[22] Filed: May 11, 1982

[30] Foreign Application Priority Data

May 20, 1981 [JP] Japan ................................ 56-76082

[51] Int. Cl.$^3$ ............................................. A61B 10/00
[52] U.S. Cl. ....................................... 128/660; 128/4
[58] Field of Search .................... 128/660, 4, 6, 661

[56] References Cited

U.S. PATENT DOCUMENTS

| | | |
|---|---|---|
| 3,779,234 | 12/1973 | Eggleton et al. .................. 128/660 |
| 4,212,207 | 7/1980 | Conradi . |
| 4,241,609 | 12/1980 | Bergman et al. . |
| 4,374,525 | 2/1983 | Baba .................... 128/660 |

FOREIGN PATENT DOCUMENTS

| | | |
|---|---|---|
| 51-23788 | 2/1976 | Japan . |
| 54-14609 | 7/1979 | Japan . |
| 56-31743 | 3/1981 | Japan . |

OTHER PUBLICATIONS

Hisanaga, K. et al., "A New Real-Time Sector Scanning System," UTS in Medicine, vol. 4, Plenun Press 1979, pp. 391-402.
Taylor, W. B. et al., "A High-Resolution Transrectal UTS System," UTS in Med. & Biol., vol. 5, #2 (1979) pp. 129-138.

*Primary Examiner*—Kyle L. Howell
*Assistant Examiner*—Francis J. Jaworski
*Attorney, Agent, or Firm*—Frishauf, Holtz, Goodman & Woodward

[57] ABSTRACT

An ultrasonic diagnostic apparatus includes an insertion section formed by a flexible elongate tube having a distal end portion and a proximal end portion. A driving shaft passes through the flexible elongate tube of the insertion section between a control section at the proximal end of the insertion section, and an ultrasonic transducer arranged for rotation at the distal end portion of the insertion section. The driving shaft includes a flexible elongate member formed by a pair of coils closely fitted coaxially one within the other. The coils have different winding directions thus providing circumferential rigidity when the driving shaft is rotated by a driving source at the control section. A signal cable is routed through the inside space of the coils forming the driving shaft and connects at one end with the transducer. The other end of the signal cable connects with a rotary terminal arrangement at the end of the driving shaft located at the control section.

8 Claims, 3 Drawing Figures

ULTRASONIC DIAGNOSTIC APPARATUS

BACKGROUND OF THE INVENTION

This invention relates to an ultrasonic diagnostic apparatus to be inserted into a body cavity for ultrasonic diagnosis.

The ultrasonic diagnostic apparatus of this type is so constructed that an ultrasonic transducer is housed in a distal end portion of an insertion section to be inserted into the body cavity, ultrasonic driving signals are transmitted from an external ultrasonic transmission-reception circuit to the ultrasonic transducer by means of a signal cable which is electrically connected with the ultrasonic transducer, and echo signals received by the ultrasonic transducer are returned to the ultrasonic transmission-reception circuit by means of the signal cable. In the case of an ultrasonic diagnostic apparatus of a mechanical-scanning type, the ultrasonic transducer need be mechanically rotated for scanning. If the ultrasonic transducer is rotated, however, the signal cable will rotate together with it and be twisted. Conventionally, therefore, the ultrasonic transducer is fixed so that ultrasonic scanning may be performed by reflecting ultrasonic waves from the ultrasonic transducer by means of a rotating mirror. According to such a rotating mirror system, only the rotating mirror need be rotated, so that the signal cable is kept from being twisted. In this case, however, the ultrasonic transducer and the rotating mirror must be contained in the distal end portion of the insertion section, so that the distal end portion will become too bulky to be inserted with ease into the body cavity.

SUMMARY OF THE INVENTION

The object of this invention is to provide an ultrasonic diagnostic apparatus, in which a signal cable is kept from being twisted as an ultrasonic transducer is rotated, and the distal end portion is reduced in size for ease of insertion into the body cavity, as compared with an apparatus of a rotating-mirror type.

DETAILED DESCRIPTION OF THE PREFERRED EMBODIMENT

There will now be described an ultrasonic diagnostic apparatus according to an embodiment of this invention with reference to the accompanying drawings.

Figure 1:
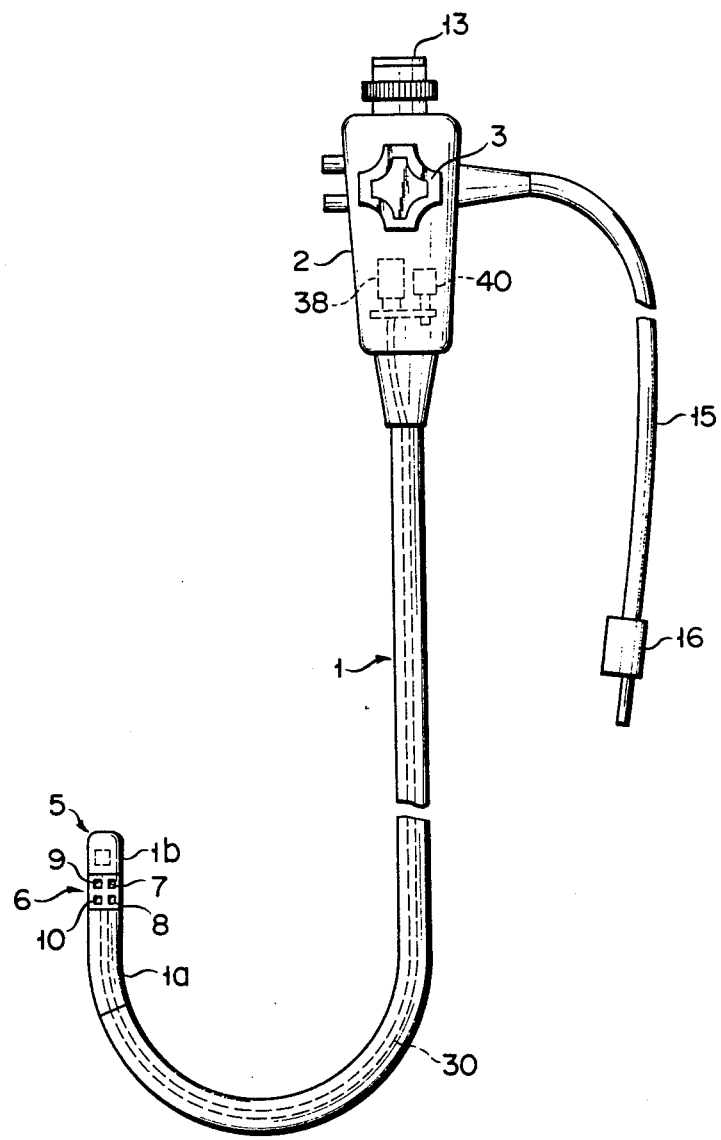
FIG. 1 is a general side view of an ultrasonic diagnostic apparatus according to an embodiment of this invention.

FIG. 1, numeral shows an insertion section 1 to be inserted into the body cavity. The insertion section 1 is formed of a flexible elongate tube which is coupled with a control section 2 on the proximal side. A bending portion 1a is formed at the distal end portion of the insertion section 1. The bending portion 1a can be bent freely with a bending control wire (not shown) by operating a bending control knob 3 at the control section 2.

Figure 2:
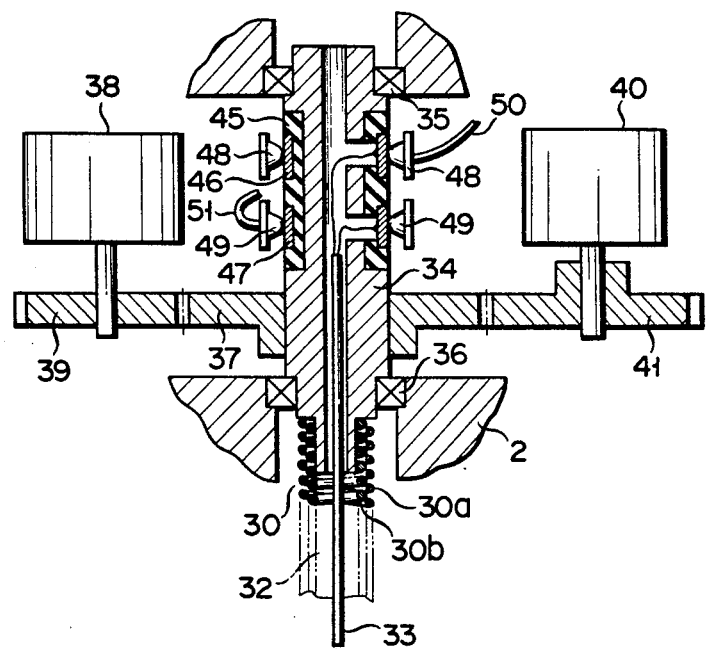
FIG. 2 is an enlarged sectional view showing part of an insertion section and part of a control section.
Figure 3:
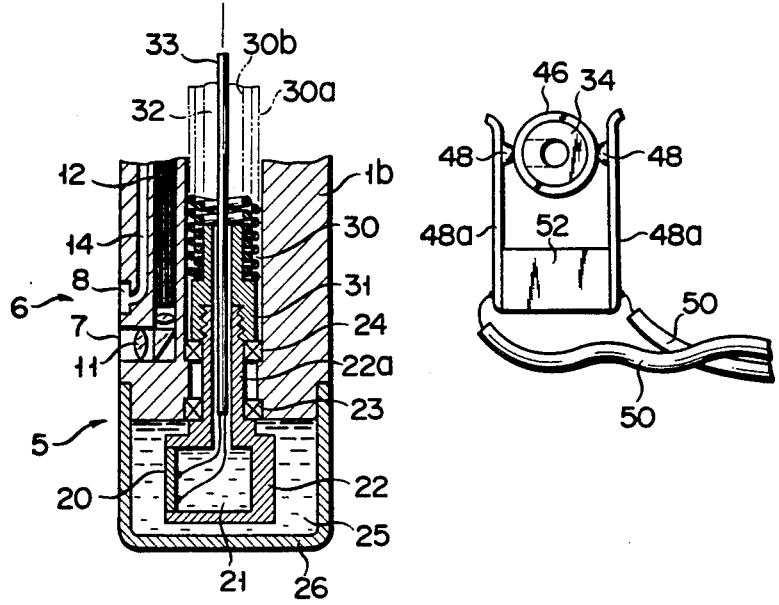
FIG. 3 is a plan view showing a rotating terminal and fixed terminals.

An ultrasonic transmission-reception scanning portion 5 and an observation window portion 6 are provided at a distal end portion 1b on the distal end side of the bending portion 1a. The observation window portion 6 is provided with an observation window 7 of an optical system for observation, an illumination window 8, an air-water nozzle 9, and an inlet port 10. As shown in FIG. 2, one end of an image guide 12 faces the inside of the observation window 7 with observation-purpose optical system members 11, including lenses, prism, etc., between them. For example, optical fibers are used for the image guide 12. The other end of the image guide 12 is led to an eyepiece portion 13 (FIG. 1) at the control section 2. The light emitting end of a light guide 14 is located inside the illumination window 8. The light guide 14 is led through the interior of the insertion section 1 and a universal cord 15 to a connector section 16 (FIG. 1), and connected with a light source unit (not shown) by means of the connector section 16.

An ultrasonic transducer 20 is housed in the ultrasonic transmission-reception scanning portion 5. The ultrasonic transducer 20 is attached to a rotor 22 with a hollow portion filled with a damper material 21. A shaft portion 22a of the rotor 22 is rotatably supported by bearings 23 and 24 so that the rotor 22 can rotate freely around the central axis of the distal end portion 1b. Formed in the distal end portion 1b is a hollow space which is filled with an ultrasonic wave propagation medium fluid 25. The rotor 22 is contained in the hollow space so that the fluid 25 is located around the rotor 22. A cap 26 is put on the tip of the distal end portion 1b to keep the hollow space liquidtight.

One end side of a hollow driving shaft 30 is coaxially fixed to the shaft portion 22a by means of a coupling member 31. The driving shaft 30 is formed of two coaxial layers of metal coils 30a and 30b closely wound with different coiling directions and is flexible, defining therein a cable insertion path 32. A signal cable 33 is passed through the cable insertion path 32. One end side of the cable 33 is electrically connected with the ultrasonic transducer 20.

The driving shaft 30 is led through the insertion section 1 to the control section 2. The other end of the driving shaft 30 is coupled with a rotating shaft 34. The rotating shaft 34 is cylindrical and is rotatably supported on the control section 2 by means of bearings 35 and 36. A gear 37 is coaxially attached to the outer peripheral surface of the rotating shaft 34. The gear 37 is in mesh with a driving gear 39 of a motor 38 so that the rotating shaft 34 can be driven to rotate by the motor 38. Further, the gear 37 is in mesh with a gear 41 of a rotation angle detector 40 so that the rotation of the driving shaft 30, that is, the scanning bearings of the ultrasonic transducer 20, can be detected.

A cylindrical electric insulator 45 is embedded in the outer peripheral surface of the rotating shaft 34, and a pair of rotating terminals 46 and 47 are embedded in the outer peripheral surface of the insulator 45. These rotating terminals 46 and 47 are isolated along the axial direction of the rotating shaft 34 so as to be electrically insulated from each other, and are formed of ring-shaped conductive members continuous along the circumferential direction of the rotating shaft 34.

Pairs of contacts or fixed terminals 48 and 49 are in contact with the outer peripheral surfaces of the rotating terminals 46 and 47, respectively. The contacts 48 and 49 protrude from the tip ends of leaf springs 48a and 49a, respectively, whose basal ends are fixed to an insulating base 52. Normally, these contacts are brought elastically in contact with the rotating terminals by means of the leaf springs. The basal ends of the leaf springs 48a and 49a are connected with conductors 50 and 51, which are connected with an ultrasonic transmission-reception circuit section (not shown). The contacts and leaf springs are formed of electric conductive material, so that the rotating terminals 46 and 47 are normally electrically connected with the conductors 50 and 51, respectively.

According to the ultrasonic diagnostic apparatus of the above-mentioned construction, an endoscopic image of the surface of the affected part or objective region can be observed through the observation window 7 by inserting the insertion section 1 into a body cavity and then looking into the eyepiece portion 13 while applying an illumination light through the illumination window 8. In ultrasonic diagnosis, the motor 38 is rotated to rotate the driving shaft 30, thereby rotating the ultrasonic transducer 20 together with the rotor 22 and actuating the ultrasonic transmission-reception circuit section (not shown). Generated ultrasonic driving signals are transmitted to the contacts 48 and 49 through the conductors 50 and 51 and the leaf springs 48a and 49a, and then transferred from the rotating terminals 46 and 47 to the ultrasonic transducer 20 by way of the signal cable 33. As a result, the ultrasonic transducer 20 is excited to emit ultrasonic waves in the radial direction of the distal end portion 1b. Since the ultrasonic transducer 20 is then rotating, ultrasonic scanning around the axis of the distal end portion 1b is performed. Echoes reflected by internal tissues of the affected part are received by the ultrasonic transducer 20. Then, the echoes are transmitted to the ultrasonic transmission-reception circuit section through the contacts 48 and 49 and the conductors 50 and 51, following the opposite course to the aforesaid one, and the transmission-reception bearings are detected by the rotation angle detector 40. An ultrasonic slice image is displayed on a display unit (not shown) by processing angle signals thus obtained, along with echo signals.

As described above, the ultrasonic transducer 20 is rotated by the driving shaft 30, and the signal cable 33 passed through the driving shaft 30 is rotated together with the driving shaft 30. Nevertheless, the signal cable 33 will not be twisted at all because it is electrically connected with the rotating terminals 46 and 47 and then to the contacts 48 and 49 which are in slide contact with the terminals 46 and 47. Since the conductive members including the rotating terminals 46 and 47 and the contacts 48 and 49 are set within the control section 2, the outside diameter of the insertion section 1 need not be increased. This may greatly facilitate miniaturization of the distal end portion 1b, in particular.

Further, the signal cable 33 is passed through the inside space of the driving shaft 30 which serves as the cable insertion path 32. Thus, the inside space of the driving shaft 30 can be utilized effectively, and the insertion section 1 can be narrowed with improved propriety. Moreover, there is no fear of the signal cable 33 hindering the rotation of the driving shaft 30.

Formed of the two layers of coils with different coiling directions, the driving shaft 30 can enjoy increased circumferential rigidity for accurate transmission of rotatary force without deteriorating its flexibility.

In the above embodiment, the contacts 48 and 49 are pressed against the rotating terminals 46 and 47 by the elastic force of the leaf springs 48a and 49a. Alternatively, for example, the contacts may be thrusted against the rotating terminals by means of other elastic members such as coil springs. In this case, the conductors 50 and 51 may be connected with the contacts directly or by means of elastic members. In the above embodiment, moreover, the rotating terminals 46 and 47 are arranged on the peripheral surface of the rotating shaft 34. Alternatively, the rotating terminals may be arranged on the end face of the rotating shaft. A single contact, instead of two, may be used for each rotating terminal.

According to this invention, as described above, an ultrasonic transducer is rotated by a hollow, flexible driving shaft one end of which is fixed to a rotor and the other end of which is led to a control section on the proximal side, a signal cable is passed through the hollow driving shaft, and rotating terminals connected with the signal cable are brought into slide contact, for electrical connection, with contacts inside the control section. Although the signal cable rotates together with the ultrasonic transducer, therefore, electrical contact can be secured without twisting the signal cable, so that the ultrasonic transducer itself can be rotated without the use of a rotating mirror or the like. Accordingly, the number of components contained in the distal end portion can be reduced to facilitate the miniaturization of the distal end portion. Since the signal cable is passed through the driving shaft, the inside space of the driving shaft can be utilized effectively, and the insertion section can be narrowed with additional propriety to improve its capability in being inserted into the body cavity.

What is claimed is:

1. An ultrasonic diagnostic apparatus, comprising:
an elongate insertion section including a flexible elongate tube having a distal end portion and a proximal end portion, for insertion into the interior of the human body with the distal end portion forward;
a control section attached to the proximal end portion of the flexible elongate tube of the insertion section;
an ultrasonic transducer arranged for rotation at the distal end portion of the flexible elongate tube of the insertion section;
a driving shaft including a flexible elongate member arranged to pass through the flexible elongate tube of the insertion section and having one end portion connected with the ultrasonic transducer and the other end portion located at the control section, the flexible elongate member comprising a pair of coils closely fitted coaxially one within the other wherein said coils have different winding directions for providing circumferential rigidity when the driving shaft is rotated;
a driving source at the control section for rotating the driving shaft to rotate the ultrasonic transducer;
a rotating member attached to the other end portion of the driving shaft at the control section, for rotation relative to the control section together with the driving shaft, the rotating member having an inside space which opens into that of the pair of coils forming the drive shaft;
a rotating terminal attached to the rotating member to rotate together with the rotating member;
a signal cable having one end portion connected with the ultrasonic transducer and the other end portion connected with the rotating terminal, wherein the signal cable passes through the inside space of the pair of coils forming the driving shaft and the inside space of the rotating member to be rotated together with the rotating member; and a fixed terminal at the control section normally in contact with the rotating terminal for providing an electrical connection between the signal cable and an external circuit for operating the ultrasonic transducer as said transducer is rotated by the driving source at the control section.

2. An ultrasonic diagnostic apparatus according to claim 1, wherein said rotating member includes a cylindrical rotating shaft rotatably disposed in the control section, and said driving source includes a motor disposed in the control section and operatively connected with the rotating shaft.

3. An ultrasonic diagnostic apparatus according to claim 2, wherein said rotating terminal includes a pair of conductive rings isolatedly provided on said rotating shaft, and said fixed terminal includes a pair of contacts severally in contact with the conductive rings.

4. An ultrasonic diagnostic apparatus according to claim 3, wherein said pair of conductive rings are axially isolated from each other on the outer periphery of the rotating shaft.

5. An ultrasonic diagnostic apparatus according to claim 4, wherein said fixed terminal includes spring means to press the pair of contact against the conductive rings.

6. An ultrasonic diagnostic apparatus according to claim 1, including a rotor for supporting the ultrasonic transducer, the rotor having a hollow shaft portion which is coaxially fixed to the distal end of the pair of coils forming the driving shaft, and bearing means fixed at the distal end portion of the flexible elongate tube of the insertion section for supporting the rotor together with the transducer for rotation about the axis of said distal end portion.

7. An ultrasonic diagnostic apparatus according to claim 1, including an observation window portion arranged at the distal end portion of the flexible elongate tube of the insertion portion, for emitting light and for forming images to be guided to the control section through the flexible elongate tube.

8. An ultrasonic diagnostic apparatus according to claim 7, wherein the observation window portion includes optical fibers for guiding the images from the window portion through the flexible elongate tube.

* * * * *